US010414803B2

(12) United States Patent
Nathwani et al.

(10) Patent No.: US 10,414,803 B2
(45) Date of Patent: Sep. 17, 2019

(54) CAPSID

(71) Applicant: UCL Business PLC, London (GB)

(72) Inventors: Amit Nathwani, London (GB); Allison Dane, London (GB)

(73) Assignee: UCL BUSINESS PLC, London (GB)

( * ) Notice: Subject to any disclaimer, the term of this patent is extended or adjusted under 35 U.S.C. 154(b) by 160 days.

(21) Appl. No.: 15/573,350

(22) PCT Filed: May 10, 2016

(86) PCT No.: PCT/GB2016/051329
§ 371 (c)(1),
(2) Date: Nov. 10, 2017

(87) PCT Pub. No.: WO2016/181123
PCT Pub. Date: Nov. 17, 2016

(65) Prior Publication Data
US 2018/0111965 A1      Apr. 26, 2018

(30) Foreign Application Priority Data
May 11, 2015   (GB) .................................. 1508026.0

(51) Int. Cl.
| C12N 15/00 | (2006.01) |
| C07K 14/005 | (2006.01) |
| C12N 15/86 | (2006.01) |
| A61K 48/00 | (2006.01) |

(52) U.S. Cl.
CPC ........ *C07K 14/005* (2013.01); *A61K 48/0008* (2013.01); *C12N 15/86* (2013.01); *C12N 2750/14122* (2013.01); *C12N 2750/14143* (2013.01)

(58) Field of Classification Search
CPC ............................. C07K 14/005; C12N 15/86
See application file for complete search history.

(56) References Cited

U.S. PATENT DOCUMENTS

| 6,156,303 A | 12/2000 | Russell et al. |
| 2003/0148506 A1 | 8/2003 | Kotin et al. |
| 2005/0287122 A1 | 12/2005 | Bartlett et al. |
| 2013/0059732 A1 | 3/2013 | Lisowski et al. |
| 2016/0289275 A1 | 10/2016 | Chiorini et al. |

FOREIGN PATENT DOCUMENTS

| JP | 2003526377 A | 9/2003 |
| WO | 9923107 A1 | 5/1999 |
| WO | 2000028004 A1 | 5/2000 |
| WO | 0168888 A2 | 9/2001 |
| WO | 02053703 A2 | 7/2002 |
| WO | 03042397 A2 | 5/2003 |
| WO | 03052051 A2 | 6/2003 |
| WO | 03092594 A2 | 11/2003 |
| WO | 2004112727 A2 | 12/2004 |
| WO | 2005033321 A2 | 4/2005 |
| WO | 2005072364 A2 | 8/2005 |
| WO | 2006066066 A2 | 6/2006 |
| WO | 2006130639 A2 | 12/2006 |
| WO | 2007089632 A2 | 8/2007 |
| WO | 2008124724 A1 | 10/2008 |
| WO | 2008145400 A2 | 12/2008 |
| WO | 2009137006 A2 | 11/2009 |
| WO | 2010093784 A2 | 8/2010 |
| WO | 2013029030 A1 | 2/2013 |
| WO | 2013063379 A1 | 5/2013 |
| WO | 2013173512 A2 | 11/2013 |
| WO | 2014052789 A1 | 4/2014 |
| WO | 2014144229 A1 | 9/2014 |
| WO | 2014193716 A2 | 12/2014 |
| WO | 2015013313 A2 | 1/2015 |
| WO | 2015054653 A2 | 4/2015 |
| WO | 2015121501 A1 | 8/2015 |
| WO | 2015126972 A1 | 8/2015 |
| WO | 2015134643 A1 | 9/2015 |
| WO | 2015168666 A2 | 11/2015 |
| WO | 2015191508 A1 | 12/2015 |
| WO | 2016065001 A1 | 4/2016 |
| WO | 2016081811 A1 | 5/2016 |
| WO | 2016133917 A1 | 8/2016 |
| WO | 2016137949 A1 | 9/2016 |
| WO | 2016141078 A1 | 9/2016 |

(Continued)

OTHER PUBLICATIONS

Berns "Parvoviridae: The viruses and their replication", Chapter 69 in Fields Virology (3d Ed. 1996.
Bowles et al. "Marker rescue of adeno-associated virus (AAV) capsid mutants: a novel approach for chimeric AAV production", Journal of Virology. Jun. 2003; 77(1): 423-432.
Cheng B et al. "Development of optimized AAV3 serotype vectors: mechanism of high-efficiency transduction of human liver cancer cells", Gene Therapy. 2012, 19: 375-384.
Choi VW et al. "AAV hybrid serotypes: Improved vectors for gene delivery", Current Gene Therapy. Jun. 2005; 5(3): 299-310.
Hauck et al. "Generation and characterization of chimeric recombinant AAV vectors", Molecular Therapy. Mar. 2003; 7(3): 419-425.
Issa PC et al. "Assessment of tropism and effectiveness of new primate-derived hybrid recombinant AAV serotypes in the mouse and primate retina", PLOS One. Apr. 2013; 8(4): 1-12.

(Continued)

*Primary Examiner* — Marcia S Noble
(74) *Attorney, Agent, or Firm* — Patent Law Works LLP

(57) ABSTRACT

There is described an AAV capsid protein having an amino acid sequence which has at least 98% identity to the sequence of SEQ ID NO: 3 or at least 94% identity to the sequence of SEQ ID NO: 4. Also described is a pharmaceutical composition, an AAV capsid and a viral particle comprising the capsid protein, a recombinant AAV vector comprising a nucleotide sequence which encodes for the capsid protein, and a host cell and a transgenic animal comprising the capsid protein or the vector. In addition, there is described a method of transferring a nucleic acid of interest into a mammal comprising introducing a recombinant AAV vector into the mammal, wherein the recombinant AAV vector comprises a gene of interest which is encapsidated into a capsid comprising the capsid protein.

6 Claims, 8 Drawing Sheets

Specification includes a Sequence Listing.

(56) References Cited

FOREIGN PATENT DOCUMENTS

| | | |
|---|---|---|
| WO | 2016154344 A1 | 9/2016 |
| WO | 2016172155 A1 | 10/2016 |
| WO | 2016210170 A1 | 12/2016 |
| WO | 2017015102 A1 | 1/2017 |
| WO | 2017023724 A1 | 2/2017 |
| WO | 2017058892 A2 | 4/2017 |
| WO | 2017066764 A2 | 4/2017 |
| WO | 2017075335 A1 | 5/2017 |
| WO | 2017075338 A2 | 5/2017 |
| WO | 2017075619 A1 | 5/2017 |
| WO | 2017077451 A1 | 5/2017 |
| WO | 2017096164 A1 | 6/2017 |
| WO | 2017100671 A1 | 6/2017 |
| WO | 2017106236 A1 | 6/2017 |
| WO | 2017143100 A1 | 8/2017 |
| WO | 2017161273 A1 | 9/2017 |
| WO | 2017180896 A1 | 10/2017 |
| WO | 2017189959 A1 | 11/2017 |
| WO | 2017189963 A1 | 11/2017 |
| WO | 2017201248 A1 | 11/2017 |
| WO | 2017216301 A1 | 12/2017 |
| WO | 2018022608 A2 | 2/2018 |
| WO | 2018035059 A1 | 2/2018 |
| WO | 2018045347 A1 | 3/2018 |
| WO | 2018046772 A1 | 3/2018 |
| WO | 2018046774 A1 | 3/2018 |
| WO | 2018046775 A1 | 3/2018 |
| WO | 2018071831 A1 | 4/2018 |
| WO | 2018081470 A1 | 5/2018 |
| WO | 2018081476 A2 | 5/2018 |
| WO | 2018152333 A1 | 8/2018 |
| WO | 2018162748 A1 | 9/2018 |
| WO | 2018170310 A1 | 9/2018 |
| WO | 2018189244 A1 | 10/2018 |
| WO | 2018200419 A1 | 11/2018 |
| WO | 2018204786 A1 | 11/2018 |
| WO | 2018204803 A1 | 11/2018 |
| WO | 2018226887 A1 | 12/2018 |
| WO | 2018232055 A1 | 12/2018 |
| WO | 2019006390 A1 | 1/2019 |
| WO | 2019025984 A1 | 2/2019 |
| WO | 2019028192 A1 | 2/2019 |
| WO | 2019028306 A2 | 2/2019 |
| WO | 2019043081 A1 | 3/2019 |
| WO | 2019060649 A1 | 3/2019 |
| WO | 2019073059 A1 | 4/2019 |

OTHER PUBLICATIONS

Lerch T et al. "Identification of the heparin binding site on adeno-associated virus serotype 3B (AAV-3B)", Virology. 2012; 423: 6-13.

Lerch T et al. "The structure of adeno-associated virus serotype 3B (AAV-3B): Insights into receptor binding and immune evasion", Virology. 2010; 403: 26-36.

Li S et al. "Efficient and Targeted Transduction of Nonhuman Primate Liver With Systemically Delivered Optimized AAV3B Vectors", Mol Ther. Dec. 2015; 23(12): 1867-76.

Ling C et al. "Strategies to generate high-titer, high-potency recombinant AAV3 serotype vectors", Molecular Therapy—Methods & Clinical Development. 2016, 3: 16029.

Ling C et al. "Human Hepatocyte Growth Factor Receptor Is a Cellular Coreceptor for Adeno-Associated Virus Serotype 3", Human Gene Therapy. Dec. 2010; 21:1741-1747.

Ling C et al. "Selective In Vivo Targeting of Human Liver Tumors by Optimized AAV3 Vectors in a Murine Xenograft Model", Human Gene Therapy. Dec. 2014; 25:1023-1034.

Lisowski et al. "Selection and evaluation of clinically relevant AAV variants in a xenograft liver model", Nature. 2014; 506: 382-386.

Manno CS et al. "Successful transduction of liver in hemophilia by AAV-Factor IX and limitations imposed by the host immune response", Nature Medicine. Mar. 2006; 12(3):342-7.

Muramatsu S et al. "Nucleotide Sequencing and Generation of an Infectious Clone of Adeno-Associated Virus 3", Virology. 1996; 221, 208-217.

Shen X et al. "Characterization of the relationship of AAV capsid domain swapping to liver transduction efficiency", Molecular Therapy. Nov. 2007; 15(11): 1955-1962.

Vercauteren K et al. "Superior in vivo Transduction of Human Hepatocytes Using Engineered AAV3 Capsid", Mol Ther. Jun. 2016; 24(6):1042-1049.

Wang L et al. "Comparative Study of Liver Gene Transfer With AAV Vectors Based on Natural and Engineered AAV Capsids", Mol Ther. Dec. 2015; 23(12): 1877-87.

PCT International Preliminary Report on Patentability, Application No. PCT/GB2016/051329, dated Nov. 14, 2017, 6 pages.

Nam et al. "Structure of Adeno-Associated Virus Serotype 8, a Gene Therapy Vector" J. Virol. (2007) Vol.81, No. 22, pp. 12260-12271.

CAPSID

CROSS-REFERENCE TO RELATED APPLICATIONS

This application is a national phase entry under 35 U.S.C. § 371 of International Patent Application PCT/GB2016/051329, filed May 10, 2016, designating the United States of America and published in English as International Patent Publication WO 2016/181123 A1 on Nov. 17, 2016, which claims the benefit under Article 8 of the Patent Cooperation Treaty to Great Britain Patent Application Serial No. 1508026.0 filed May 11, 2015.

STATEMENT ACCORDING TO 37 C.F.R. § 1.821(c) or (e)—SEQUENCE LISTING SUBMITTED AS ASCII TEXT FILE

Pursuant to 37 C.F.R. § 1.821(c) or (e), a file containing an ASCII text version of the Sequence Listing has been submitted concomitant with this application, the contents of which are hereby incorporated by reference.

FIELD OF THE INVENTION

The invention relates to adeno-associated virus (AAV) capsid variants.

BACKGROUND TO THE INVENTION

Multiple recombinant gene transfer vectors based on different viruses have been developed in recent years. Gene transfer vectors based on adeno-associated virus (AAV), i.e., AAV vectors, are preferred due to their ability to transduce different types of dividing and non-dividing cells of different tissues and the ability to establish stable, long-term transgene expression. While vectors based on other viruses, such as adenoviruses and retroviruses may possess certain desirable characteristics, they have also been associated with undesirable side effects. Such side effects have not been detected with gene transfer vectors based on AAV (Manno et al., Nature Medicine, 12(3):342 (2006)).

Many AAV serotypes have been identified, cloned, sequenced, and converted into vectors. These serotypes include AAV8, AAV5, AAV3B and the more recently described AAV-LK03 (WO 2013/029030). However, the present inventors have found that many of the currently used vectors have a low transduction rate in humans. For example, AAV8 vectors have a 20-fold lower transduction in humans than in mice as well as transient, prednisolone responsive, transaminitis which occurred in two-thirds of a high dose cohort. Thus, a need remains for new AAV vectors to improve potency and safety, as well as promoting wider clinical applicability.

To this end, the inventors have developed new hybrid capsids by empirically swapping various domains from 4 different AAV capsids: (1) AAV8, (2) AAV5, (3) AAV3B, and (4) AAV-LK03. Capsids were developed which achieved up to a 5-fold higher level of gene transfer than currently used vectors.

SUMMARY OF THE INVENTION

In a first aspect of the invention, there is provided an AAV capsid protein having an amino acid sequence which has at least 98% identity to SEQ ID NO: 3 or at least 94% identity to SEQ ID NO: 4.

The inventors have surprisingly found that the novel capsid protein produces a capsid which provides a higher transduction rate than currently used AAV vectors. Further, it has been found that the prevalence of antibodies to the capsid in patients is lower than for some currently used AAV vectors.

In some embodiments, the amino acid sequence has at least 95% identity to the sequence of SEQ ID NO: 4. In particular embodiments, the amino acid sequence has at least 96% identity to the sequence of SEQ ID NO: 4. In further embodiments, the amino acid sequence has at least 97% identity to the sequence of SEQ ID NO: 4. In some embodiments, the amino acid sequence has at least 98% identity to the sequence of SEQ ID NO: 4. In other embodiments, the amino acid sequence has at least 99% identity to the sequence of SEQ ID NO: 4. In particular embodiments, the amino acid sequence has the sequence of SEQ ID NO: 4.

In some embodiments, the amino acid sequence has at least 98.5% identity to the sequence of SEQ ID NO: 3, preferably at least 99% identity to the sequence of SEQ ID NO: 3 and more preferably at least 99.5% identity to the sequence of SEQ ID NO: 3. In particular embodiments, the amino acid sequence has the sequence of SEQ ID NO: 3.

In some embodiments, the amino acid sequence has identity to the sequence of SEQ ID NO: 3. In other embodiments, the amino acid sequence has identity to the sequence of SEQ ID NO: 4. In preferred embodiments, the amino acid sequence has the sequence of SEQ ID NO: 4. More preferably, the amino acid sequence has the sequence of SEQ ID NO: 3.

The capsid protein having the amino acid sequence defined above is a functional capsid protein which can form a functional capsid, along with other necessary capsid proteins. A functional capsid is one which can enclose genetic material, enter a cell and transduce the cell with the genetic material. It would be well within the capabilities of a skilled person to determine whether a capsid is functional. For example, the experiments described below in the detailed description of the invention can be used to determine whether a capsid can successfully transduce a cell.

SEQ ID NO: 3 is generated by cloning a 146 amino acid region encompassing the AAV8 VP1 region upstream of the VP2 and VP3 domains of the AAV3B capsid. SEQ ID NO: 4 is generated by cloning the AAV5 VP1 region upstream of the AAV3B VP2 and VP3 regions. Further details of AAV serotypes and capsid proteins is provided below.

A second aspect of the invention provides an AAV capsid comprising the AAV capsid protein described above. An AAV capsid is a protein shell made up of VP1, VP2 and VP3 proteins and which encapsidates (or encloses) the genetic material of the virus.

Further, there is provided a viral particle comprising the AAV capsid protein described above. The viral particle comprises the AAV capsid and the genetic material of the virus.

In a third aspect of the invention, there is provided a recombinant AAV (rAAV) vector comprising a nucleotide sequence which encodes for the amino acid sequence described above. This means that the vector contains a nucleotide sequence encoding for a functional capsid protein.

Preferably the vector further comprises a promoter such that the nucleotide sequence is expressible. Preferably the vector comprises the AAV2 p40 viral promoter, which is constitutionally active in most mammalian cell types.

Accordingly, the present invention provides gene delivery vectors based on adeno-associated virus (AAV), which normally infects humans (e.g., serotypes 1, 2, 3A, 3B, 4, 5, and 6) or primates (e.g., serotypes 1 and 4). Further information on this virus is described in Kenneth I. Berns, "Parvoviridae: The Viruses and Their Replication," Chapter 69 in Fields Virology (3d Ed. 1996).

The genomic organization of all known AAV serotypes is very similar. The genome of AAV is a linear, single-stranded DNA molecule that is less than about 5,000 nucleotides (nt) in length. Inverted terminal repeats (ITRs) flank the unique coding nucleotide sequences for the non-structural replication (Rep) proteins and the structural (VP) proteins. The VP proteins (VP1, VP2 and VP3) form the capsid. The terminal 145 nt are self-complementary and are organized so that an energetically stable intramolecular duplex forming a T-shaped hairpin may be formed. These hairpin structures function as an origin for viral DNA replication, serving as primers for the cellular DNA polymerase complex. Following wild type (wt) AAV infection in mammalian cells the Rep genes (i.e. encoding Rep78 and Rep52 proteins) are expressed from the P5 promoter and the P19 promoter, respectively, and both Rep proteins have a function in the replication of the viral genome. A splicing event in the Rep ORF results in the expression of actually four Rep proteins (i.e. Rep78, Rep68, Rep52 and Rep40). However, it has been shown that the unspliced mRNA, encoding Rep78 and Rep52 proteins, in mammalian cells are sufficient for AAV vector production. Also in insect cells the Rep78 and Rep52 proteins suffice for AAV vector production.

In an AAV suitable for use as a gene therapy vector, the vector genome typically comprises a nucleic acid of interest to be packaged for delivery to a target cell. According to this particular embodiment, the nucleic acid is located between the viral ITRs at either end of the vector genome. It is possible for an AAV genome to function with only one ITR. Thus, in a gene therapy vector of the invention based on AAV, the vector genome is flanked by at least one ITR, but, more typically, by two AAV ITRs (generally with one either side of the vector genome, i.e. one at the 5' end and one at the 3' end). There may be intervening sequences between the nucleic acid in the vector genome and one or more of the ITRs.

In the context of the invention "at least one ITR" is understood to mean a palindromic sequence, comprising mostly complementary, symmetrically arranged sequences also referred to as "A," "B," and "C" regions. The ITR functions as an origin of replication, a site having a "cis" role in replication, i.e., being a recognition site for trans-acting replication proteins such as e.g. Rep 78 (or Rep68) which recognize the palindrome and specific sequences internal to the palindrome. One exception to the symmetry of the ITR sequence is the "D" region of the ITR. It is unique (not having a complement within one ITR). Nicking of single-stranded DNA occurs at the junction between the A and D regions. It is the region where new DNA synthesis initiates. The D region normally sits to one side of the palindrome and provides directionality to the nucleic acid replication step. An AAV replicating in a mammalian cell typically has two ITR sequences. It is, however, possible to engineer an ITR so that binding sites are on both strands of the A regions and D regions are located symmetrically, one on each side of the palindrome. On a double-stranded circular DNA template (e.g., a plasmid), the Rep78- or Rep68-assisted nucleic acid replication then proceeds in both directions and a single ITR suffices for parvoviral replication of a circular vector. Thus, one ITR nucleotide sequence can be used in the context of the present invention. Preferably, however, two or another even number of regular ITRs are used. Most preferably, two ITR sequences are used. For safety reasons it may be desirable to construct an AAV vector that is unable to further propagate after initial introduction into a cell. Such a safety mechanism for limiting undesirable vector propagation in a recipient may be provided by using AAV with a chimeric ITR as described in US 2003148506.

Those skilled in the art will appreciate that the viral Rep protein(s) used for producing an AAV vector of the invention may be selected with consideration for the source of the viral ITRs. For example, the AAV5 ITR typically interacts more efficiently with the AAV5 Rep protein, although it is not necessary that the serotype of ITR and Rep protein(s) are matched.

The ITR(s) used in the invention are typically functional, i.e. they may be fully resolvable and are AAV sequences, with serotypes 1, 2, 3, 4, 5 or 6 being preferred. Resolvable AAV ITRs according to the present invention need not have a wild-type ITR sequence (e. g., a wild-type sequence may be altered by insertion, deletion, truncation or missense mutations), as long as the ITR mediates the desired functions, e.g., virus packaging, integration, and/or provirus rescue, and the like.

In further preferred embodiments, the AAV cap genes and AAV rep genes are deleted from the template genome (and thus from the virion DNA produced therefrom). This configuration maximizes the size of the nucleic acid sequence(s) that can be carried by the AAV capsid.

AAV sequences that may be used in the present invention for the production of AAV gene therapy vectors can be derived from the genome of any AAV serotype. Generally, the AAV serotypes have genomic sequences of significant homology at the amino acid and the nucleic acid levels, provide an identical set of genetic functions, produce virions which are essentially physically and functionally equivalent, and replicate and assemble by practically identical mechanisms. For the genomic sequence of the various AAV serotypes and an overview of the genomic similarities see e.g. GenBank Accession number U89790; GenBank Accession number J01901; GenBank Accession number AF043303; GenBank Accession number AF085716. AAV serotype 1, 2, 3, 4, 5, 6, 7, 8 or 9 may be used in the present invention. However, AAV serotypes 1, 5 or 8 are preferred sources of AAV sequences for use in the context of the present invention. The sequences from the AAV serotypes may be mutated or engineered when being used in the production of gene therapy vectors.

Preferably, the AAV ITR sequences for use in the context of the present invention are derived from AAV1, AAV2, AAV4 and/or AAV6. Likewise, the Rep (Rep78 and Rep52) coding sequences are preferably derived from AAV1, AAV2, AAV4 and/or AAV6.

AAV Rep and ITR sequences are particularly conserved among most serotypes. The Rep78 proteins of various AAV serotypes are e.g. more than 89% identical and the total nucleotide sequence identity at the genome level between AAV2, AAV3A, AAV3B, and AAV6 is around 82%. Moreover, the Rep sequences and ITRs of many AAV serotypes are known to efficiently cross-complement (i.e., functionally substitute) corresponding sequences from other serotypes in production of AAV particles in mammalian cells. US 2003148506 reports that AAV Rep and ITR sequences also efficiently cross-complement other AAV Rep and ITR sequences in insect cells.

The AAV VP proteins are known to determine the cellular tropicity of the AAV virion. The VP protein-encoding sequences are significantly less conserved than Rep proteins and genes among different AAV serotypes. The ability of Rep and ITR sequences to cross-complement corresponding sequences of other serotypes allows for the production of pseudotyped AAV particles comprising the capsid proteins of a serotype (e.g., AAV1, 5 or 8) and the Rep and/or ITR sequences of another AAV serotype (e.g., AAV2). Such pseudotyped rAAV particles are part of the present invention as the Rep and/or ITR sequences of any AAV serotype can be used with the modified capsid protein of the invention.

Modified "AAV" sequences also can be used in the context of the present invention, e.g. for the production of AAV gene therapy vectors. Such modified sequences e.g. include sequences having at least about 70%, at least about 75%, at least about 80%, at least about 85%, at least about 90%, at least about 95%, or more nucleotide and/or amino acid sequence identity (e.g., a sequence having about 75-99% nucleotide sequence identity) to an AAV1, AAV2, AAV3, AAV4, AAV5, AAV6, AAV7, AAV8 or AAV9 ITR, or Rep can be used in place of wild-type AAV ITR, or Rep sequences.

Although similar to other AAV serotypes in many respects, AAV5 differs from other human and simian AAV serotypes more than other known human and simian serotypes. In view thereof, the production of rAAV5 can differ from production of other serotypes in insect cells. Where methods of the invention are employed to produce rAAV5, it is preferred that one or more constructs comprising, collectively in the case of more than one construct, a nucleotide sequence comprising an AAV5 ITR, a nucleotide sequence comprises an AAV5 Rep coding sequence (i.e. a nucleotide sequence comprises an AAV5 Rep78). Such ITR and Rep sequences can be modified as desired to obtain efficient production of AAV5 or pseudotyped AAV5 vectors.

It is within the technical skills of the skilled person to select the most appropriate virus, virus subtype or virus serotype. Some subtypes or serotypes may be more appropriate than others for a certain type of tissue.

For example, liver-specific expression of a nucleic acid of interest may advantageously be induced by AAV-mediated transduction of liver cells. Liver is amenable to AAV-mediated transduction, and different serotypes may be used (for example, AAV1, AAV5 or AAV8). Transduction of muscle may be accomplished by administration of an AAV encoding a nucleic acid via the blood stream. Thus, intravenous or intra-arterial administration is applicable.

Advantageously, by using the vector of the present invention, a greater degree of cellular transduction can be obtained. This is particularly the case in liver cells.

Accordingly, the vectors of the invention therefore represent a tool for the development of strategies for the in vivo delivery of a therapeutic nucleotide sequence, by engineering the nucleic acid within a gene therapy vector that efficiently transduces an appropriate cell type, such as a liver cell.

The vector may comprise other elements to allow the functional therapeutic protein to be expressed. Such elements are well known to a person skilled in the art.

Preferably, the nucleic acids and amino acid sequences described above are isolated.

It would be well with the capabilities of a skilled person to produce the nucleic acid molecules and amino acid sequences described above. This could be done, for example, using chemical synthesis of a given sequence.

The invention also relates to a method of transferring a nucleic acid of interest into a mammal comprising introducing a recombinant AAV vector into a mammal, the recombinant AAV vector comprising a gene of interest which is encapsidated into a capsid comprising the capsid protein described above.

The invention also provides a host cell comprising the capsid protein having the amino acid sequences described above or the vectors described above.

As used herein, the term "host" refers to organisms and/or cells which harbour a protein or a vector of the invention, as well as organisms and/or cells that are suitable for use in expressing a recombinant gene or protein. It is not intended that the present invention be limited to any particular type of cell or organism. Indeed, it is contemplated that any suitable organism and/or cell will find use in the present invention as a host. A host cell may be in the form of a single cell, a population of similar or different cells, for example in the form of a culture (such as a liquid culture or a culture on a solid substrate), an organism or part thereof.

A host cell according to the invention may permit the expression of a therapeutic nucleic acid molecule. Thus, the host cell may be, for example, a bacterial, a yeast, an insect or a mammalian cell.

In addition, the invention provides a transgenic animal comprising cells comprising the capsid protein having the amino acid sequence described above or a vector described above. Preferably the animal is a non-human mammal, especially a primate. Alternatively, the animal may be a rodent, especially a mouse; or may be canine, feline, ovine or porcine.

In one aspect, the invention provides a pharmaceutical composition comprising the capsid protein having the amino acid sequence of the present invention or a vector of the invention and one or more pharmaceutically acceptable excipients. The one or more excipients include carriers, diluents and/or other medicinal agents, pharmaceutical agents or adjuvants, etc.

The higher levels of gene transfer achieved with the sequences of the present invention represents an advance beyond the current state of the art. An improvement in potency has been observed which will permit gene transfer using lower vector doses, thus improving safety (especially reducing liver toxicity which is dose dependent) and at a lower cost. Accordingly the sequences and vector of the present invention may have a clinical applicability to disorders such as congenital FVII deficiency, Gaucher's disease, OTC deficiency, Fabry's disease, glycogen storage diseases, α-1-antitrypsin deficiency, progressive familial intrahepatic cholestasis, Wilson's disease, Crigler Najjar syndrome and hepatocellular carcinoma amongst others.

Accordingly, the invention may provide a method of treating one or more of the diseases listed above comprising administering a therapeutically effective amount of a vector as described above to a patient suffering from said disease. Preferably, the patient is human.

When said disease is "treated" in the above method, this means that one or more symptoms of said disease are ameliorated. It does not mean that the symptoms of said disease are completely remedied so that they are no longer present in the patient, although in some methods, this may be the case. The method of treating results in one or more of the symptoms of said disease being less severe than before treatment.

A "therapeutically effective amount" refers to an amount effective, at dosages and for periods of time necessary, to achieve the desired therapeutic result.

Further, the invention may provide the capsid protein as described above, or a vector as described above for use in therapy, preferably for one of the afore-mentioned diseases.

In addition, the invention may provide for the use of the capsid protein as described above or a vector as described above in the manufacture of a medicament for treating one of the diseases as mentioned above.

In the description above, the term "identity" is used to refer to the similarity of two sequences. For the purpose of this invention, it is defined here that in order to determine the percent identity of two amino acid sequences, the sequences are aligned for optimal comparison purposes (e.g., gaps can be introduced in the sequence of a amino acid for optimal alignment with a second amino acid sequence). The amino acid residues are then compared. When a position in the first sequence is occupied by the same amino acid or amino acid residue as the corresponding position in the second sequence, then the molecules are identical at that position. The percent identity between the two sequences is a function of the number of identical positions shared by the sequences (i.e., % identity=number of identical positions/total number of positions (i.e. overlapping positions)×100). Preferably, the two sequences are the same length.

A sequence comparison may be carried out over the entire lengths of the two sequences being compared or over fragment of the two sequences. Typically, the comparison will be carried out over the full length of the two sequences being compared. However, sequence identity may be carried out over a region of, for example, about twenty, about fifty, about one hundred, about two hundred, about five hundred, about 1000 or about 2000 or more contiguous amino acid residues.

The skilled person will be aware of the fact that several different computer programs are available to determine the homology or identity between two sequences. In preferred embodiments, the identity between two sequences is analysed using the software package Clone Manager Professional version 9 (preferably, version 9.4). This analysis tool is produced by Sci-Ed Software (Scientific & Educational Software, 11010 Lake Grove Blvd, Ste 100, PMB 122, Morrisville, N.C. 27560, USA—http://www.scied.com/index.htm). The settings used to compare the sequences are preferably as follows: alignment: Global DNA alignment; parameters: both strands; scoring matrix: linear (mismatch 2, OpenGap 4, ExtGap 1). Alternatively methods such as Fast Scan—MaxScore and Fast Scan MaxQual can also be used with the same software and local settings.

Other methods can also be used to determine sequence identity. For example, the percent identity between two amino acid or nucleic acid sequences can be determined using the Needleman and Wunsch (1970) algorithm which has been incorporated into the GAP program in the Accelrys GCG software package (available at http://www.accelrys.com/products/gcg/), using either a Blosum 62 matrix or a PAM250 matrix, and a gap weight of 16, 14, 12, 10, 8, 6, or 4 and a length weight of 1, 2, 3, 4, 5, or 6.

All patent and literature references cited in the present specification are hereby incorporated by reference in their entirety.

A skilled person will appreciate that all aspects of the invention, whether they relate to, for example, the amino acid, the viral particle, vector, the host cell or the use, are equally applicable to all other aspects of the invention. In particular, aspects of the method of treatment, for example, the administration of the vector, may have been described in greater detail than in some of the other aspects of the invention, for example, relating to the use of the vector in therapy. However, the skilled person will appreciate where more detailed information has been given for a particular aspect of the invention, this information is generally equally applicable to other aspects of the invention. Further, the skilled person will also appreciate that the description relating to the method of treatment is equally applicable to the use of vector in therapy.

DETAILED DESCRIPTION OF THE INVENTION

The invention will now be described in detail by way of example only with reference to the figures in which:

FIG. 1 shows the evaluation of hybrid AAV capsids. Part A shows a schematic of the hybrid capsids and part B illustrates the in vitro transfer efficiency of the different hybrid capsids at two different MOIs (Multiplicity of Infections) in HUH7 cells.

FIG. 2 shows the results of cell transduction experiments. FIG. 2A shows the results of transduction of HUH7 cells with AAV8, AAV5, AAV-rh10, AAV-LK03 and AAV Mutant C vectors. FIG. 2B shows the results of transduction of adherent HepG2 cells with AAV8, AAV5, AAV-LK03 and AAV Mutant C vectors.

The inventors' research program was designed to establish an AAV vector which has a relatively high transduction rate and minimal side effects. As a result, the inventors have developed new hybrid capsids and vectors.

Example 1

Figure 1:
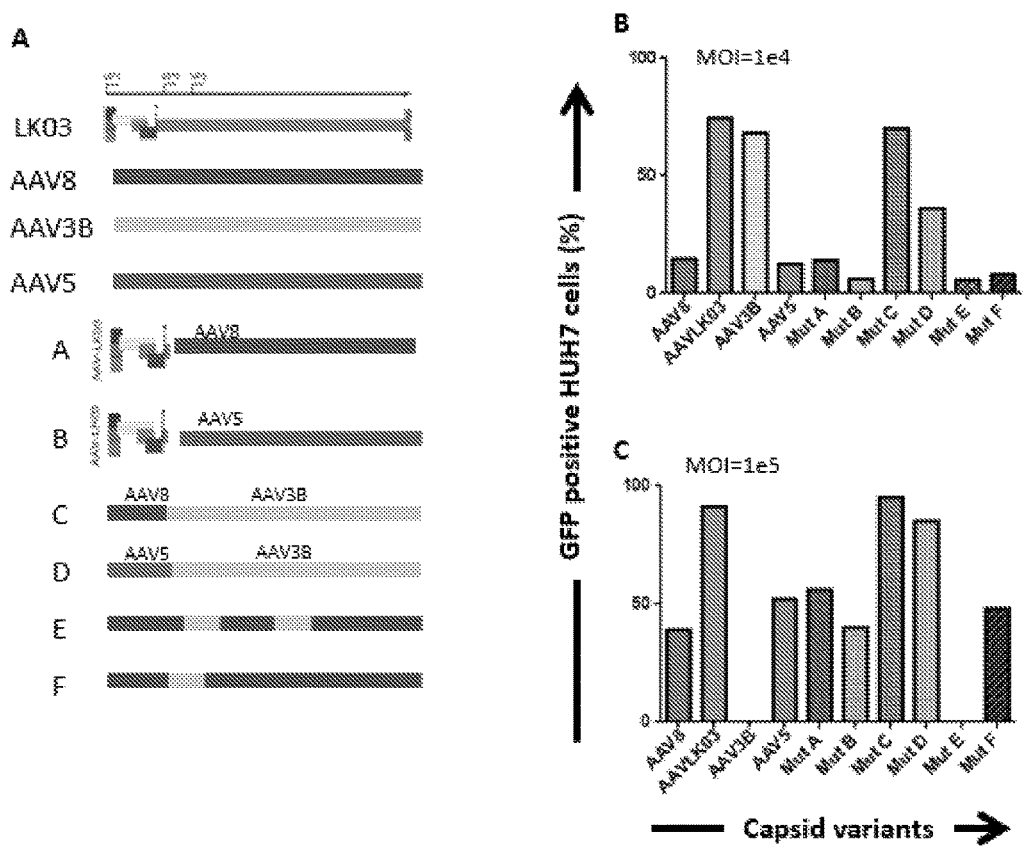

New hybrid capsids were generated by empirically swapping various domains from 4 different AAV capsids: (1) AAV8, (2) AAV5, (3) AAV3B, and (4) AAV-LK03 (see FIG. 1). The latter has been reported to transduce human hepatocytes more efficiently than the currently available naturally occurring AAV capsids. Notably, LK03 has >95% amino acid sequence homology with AAV3B. The capsid protein of the present invention is a synthetic capsid that has been developed by selection of motifs from wild type AAV capsids from serotypes 1-rh10. The VP2 and VP3 regions of LK03 were replaced with corresponding regions from AAV8 and AAV5 to generate mutants A (SEQ ID NO: 1) (Mut A) and B (SEQ ID NO: 2) (Mut B) respectively. In mutant C (SEQ ID NO: 3) (Mut C), a 146 amino acid region encompassing the AAV8 VP1 region was cloned upstream of the VP2 and VP3 domains of the AAV3B capsid. Similarly, in mutant D (SEQ ID NO: 4) (Mut D) the AAV5-VP1 region was cloned upstream of the AAV3B VP2 and VP3 regions. In mutant E (SEQ ID NO: 5) (Mut E), domains v-I, v-II, and v-IX of AAV8 were replaced with cognate from AAV3B. In mutant F (SEQ ID NO: 6) (Mut F), a 262 amino acid region containing the hepatocyte growth factor receptor binding site of AAV3B was cloned into the corresponding region of the AAV8 capsid.

The ratio of VP1, VP2 and VP3 for the synthetic capsids, in particular mutant C and mutant D, is similar to that observed for AAV2, 3b, 5 or 8. Both mutant C and mutant D have a strong tropism for human liver cells and are able to mediate higher levels of gene transfer into these cells when compared to wild type AAV capsids including AAV5 and AAV8.

The capsid sequences were assembled by overlapping PCR or generated by gene synthesis (GenScript; Mut C, Mut E and F). The capsid sequences were cloned into an AAV helper plasmid containing the Rep78 coding sequence of AAV2 which has a modified start codon (ATG to ACG). Vector stocks were prepared by standard triple plasmid transfection of HEK293 cells with pCMV-eGFP, pRep2Cap and the adenoviral helper plasmid, pHGTI. Vector was purified by density gradient centrifugation with iodixanol. Vector genomes were titered by QPCR with primers specific for eGFP. The yield of the hybrid AAV vectors was comparable to that previously observed with AAV8. Gene transfer efficiency of these hybrid capsids was assessed in vitro using the HUH7 hepatocellular carcinoma cell line at multiplicity of infection (MOI) $1\times10^4$ and $1\times10^5$. Level of gene transfer was determined by detection of the reporter gene, eGFP, by flow cytometry. The highest level of gene transfer was achieved with mutant C at levels that were at least 5-fold higher than AAV8 (FIG. 1B). This mutant mediated similar levels of gene transfer as AAV3B and novel serotype LK03. Efficiency of gene transfer of mutant D was lower than that of mutant C but 3-fold higher than parental serotype, AAV5. Mutants E and F had much lower levels of gene transfer when compared to mutant C with similar levels of GFP positive cells as seen with wild type AAV8 and AAV5.

Example 2

Production of recombinant AAV vectors. AAV vectors were made by co-transfection of adherent HEK293 T-cells with a combination of plasmids consisting of the vector plasmid in which the EGFP reporter gene was under the control of CMV promoter, an adenoviral helper plasmid, and a packaging plasmids in which the respective AAV cap gene was downstream of AAV2 Rep gene under the control of the endogenous promoters. Vectors were purified using AVB column chromatography. Titration of all vectors was performed by qPCR assay as well as alkaline gel analysis.

In-vitro transduction. Liver cancer cell lines grown in monolayer were transduced with AAV at various MOI's followed by assessment of transduction efficiency using flow cytometry at ~72 hours after gene transfer.

Primary human hepatocytes were obtained from Lifetechnologies and maintained in culture as per supplier's instruction. They were then exposed to AAV encoding GFP under the CMV promoter. Gene transfer efficiency was assessed 3-4 days later using either flow cytometry or direct fluorescent microscopy.

3D cultures of encapsulated HepG2 cells were exposed to different MOI's of AAV followed by assessment of by quantify green fluorescence using a plate reader or by direct fluorescent microscopy.

Anti-AAV-antibody titre. An immunoabsorption method was used to assess anti-AAV antibody titre in plasma samples obtained from severe haemophilia patients. Anti-AAV antibody titres were expressed as the end-point titre (Relative units/ml) defined as the reciprocal of the interpolated dilution with an absorbance value equal to five times the mean absorbance background value.

Transduction Efficiency of AAV Mutant C Vectors Compared to Other Serotypes in Human Liver Cells Lines and Primary Human Hepatocytes In a focused study, the in vitro transduction efficiency of AAV8, AAV5, AAV-rh10, AAV-LK03 and AAV Mut C in Huh7 (liver cancer cell line) and HepG2 cell lines (liver cancer cell line) was compared. All vectors contained the green fluorescent protein (GFP) reporter gene under the control of the cytomegalovirus (CMV) promoter.

Figure 2A:
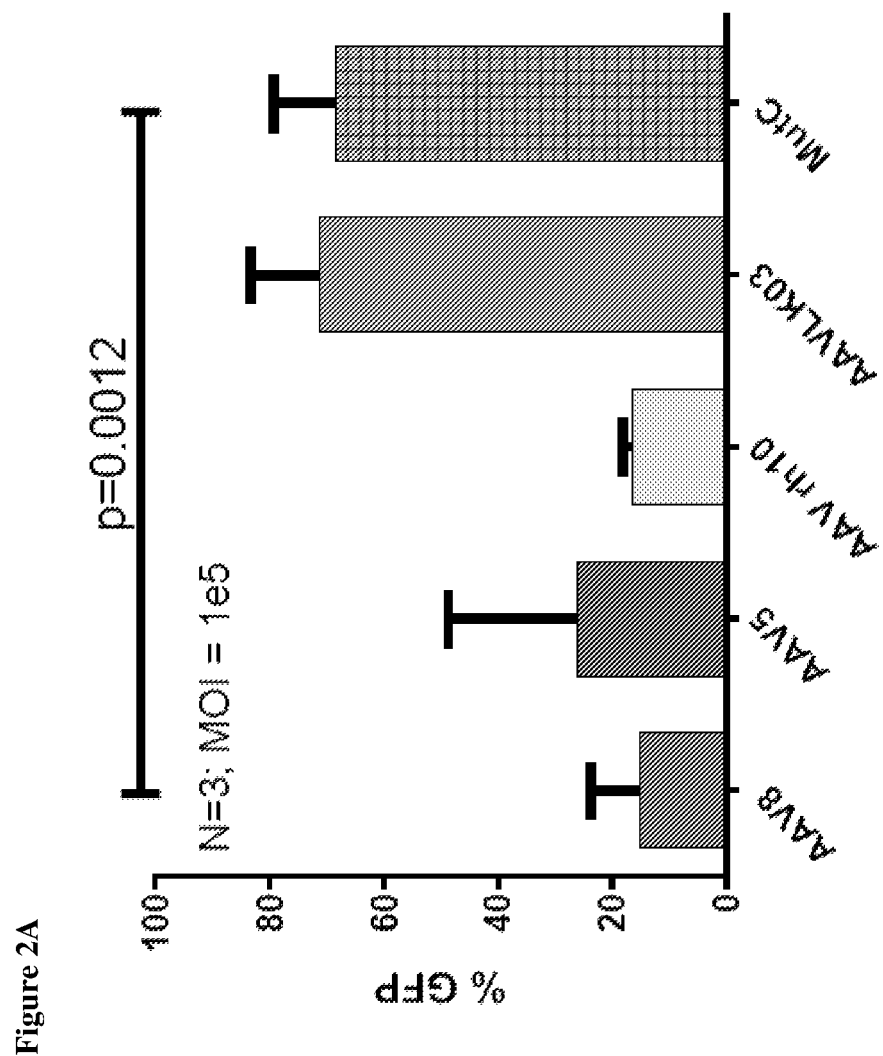

AAV8, AAV5 and AAV-rh10 vectors were less efficient at transducing Huh7 cells with mean GFP expression ranging from 15%-26%. In comparison higher levels of gene transfer were observed with AAV-LK03, and Mut C with transduction efficiency approaching 70% for vectors pseudotyped with these capsid proteins (FIG. 2A). The difference in gene transfer efficiency between Mut C and AAV8 was highly significant (p=0.0012).

Figure 2B:
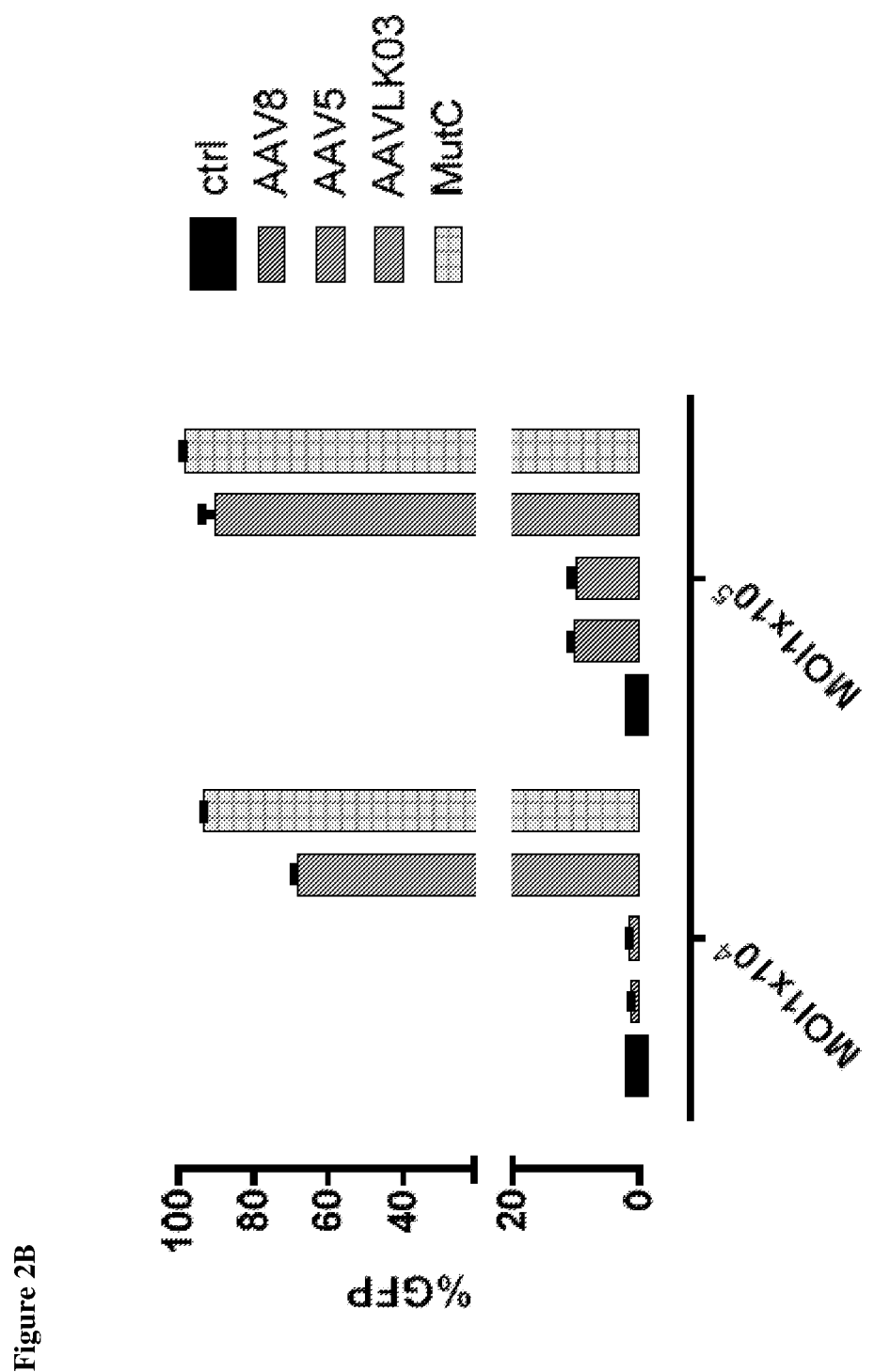

Similar results were obtained in the HepG2 cell line (FIG. 2B) with almost 10 fold higher gene transfer efficiency observed when HepG2 cells were transduced with AAV Mut C and AAV-LK03 when compared to AAV8 and AAV5, irrespective of MOI (P=<0.05).

Figure 3A:
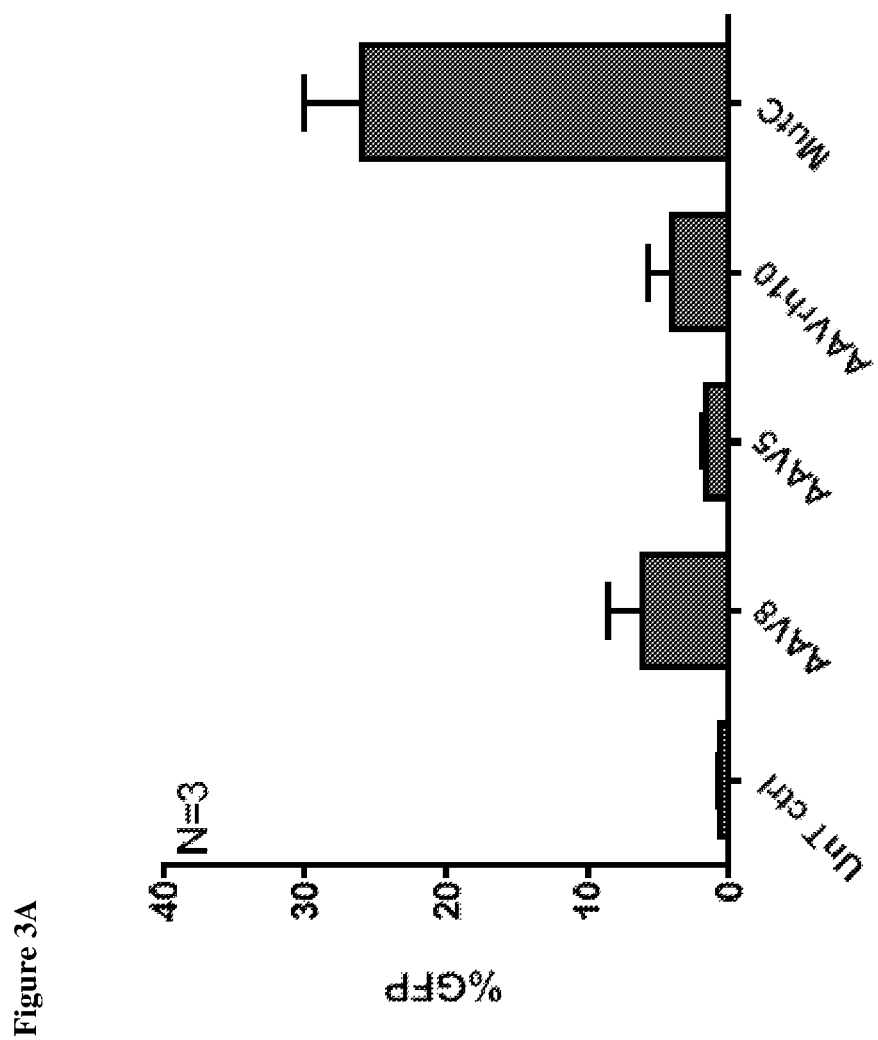
FIG. 3A shows the flow-cytometric analysis of the transduction of primary hepatocytes with AAV8, AAV5, AAV-rh10 and AAV Mutant C vectors.
Figure 3B:
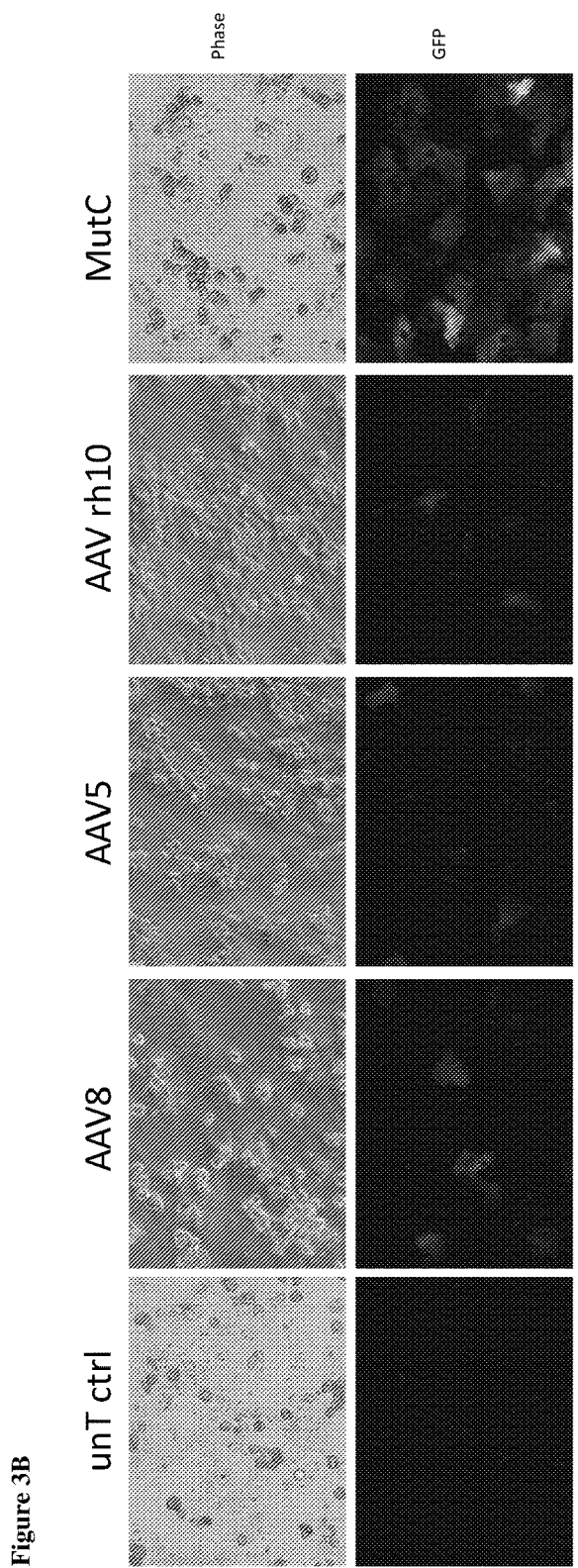
FIG. 3B is fluorescent microscope images of the transduced hepatocytes.

Next gene transfer efficiency of primary human hepatocytes derived from 3 different donors was assessed. All donors were male with 2 being of Caucasian origin and 1 of Afro-Caribbean origin. The age of these donors ranged from 21-52 years. Primary hepatocytes were exposed to AAV vector at an MOI of $10^6$ using a vector encoding GFP under the control of CMV promoter. Transduction efficiency was assessed by fluorescent microscopy or flow cytometry at 4-5 days after gene transfer. As shown in FIG. 3, gene transfer efficiency achieved with AAV Mut C (32.06±4%) was more than 4× higher than that achieved with AAV8 (7.3±7%). The difference in gene transfer efficiency of primary human hepatocytes between AAV Mut C and AAV8 groups was highly significant (p=0.0015 using 1 sample t-test). Direct fluorescent image analysis validated the flow cytometric data showing a much higher level of GFP expression in the cells transduced with AAV Mut C (FIG. 3B).

The inventors next looked at AAV mediated gene transfer into 3D cultures of HepG2 cells encapsulated in alginate using a JetCutter to produce approximately 500 μm spherical beads containing HepG2 cells at an approximate concentration of 1.7M per ml beads. The strength of this model is that within the beads encapsulated cells proliferate to form compact cell spheroids (AELS) with good cell to cell contact and cell function. AELS exhibit better growth and upregulated liver specific function compared to monolayer cultures, with typical cell architecture demonstrating desmosomes, tight junctions and micro-villi, high representation of endoplasmic reticulum and mitochondria, and generation of extracellular matrix reminiscent of that in normal liver.

Figure 4A:
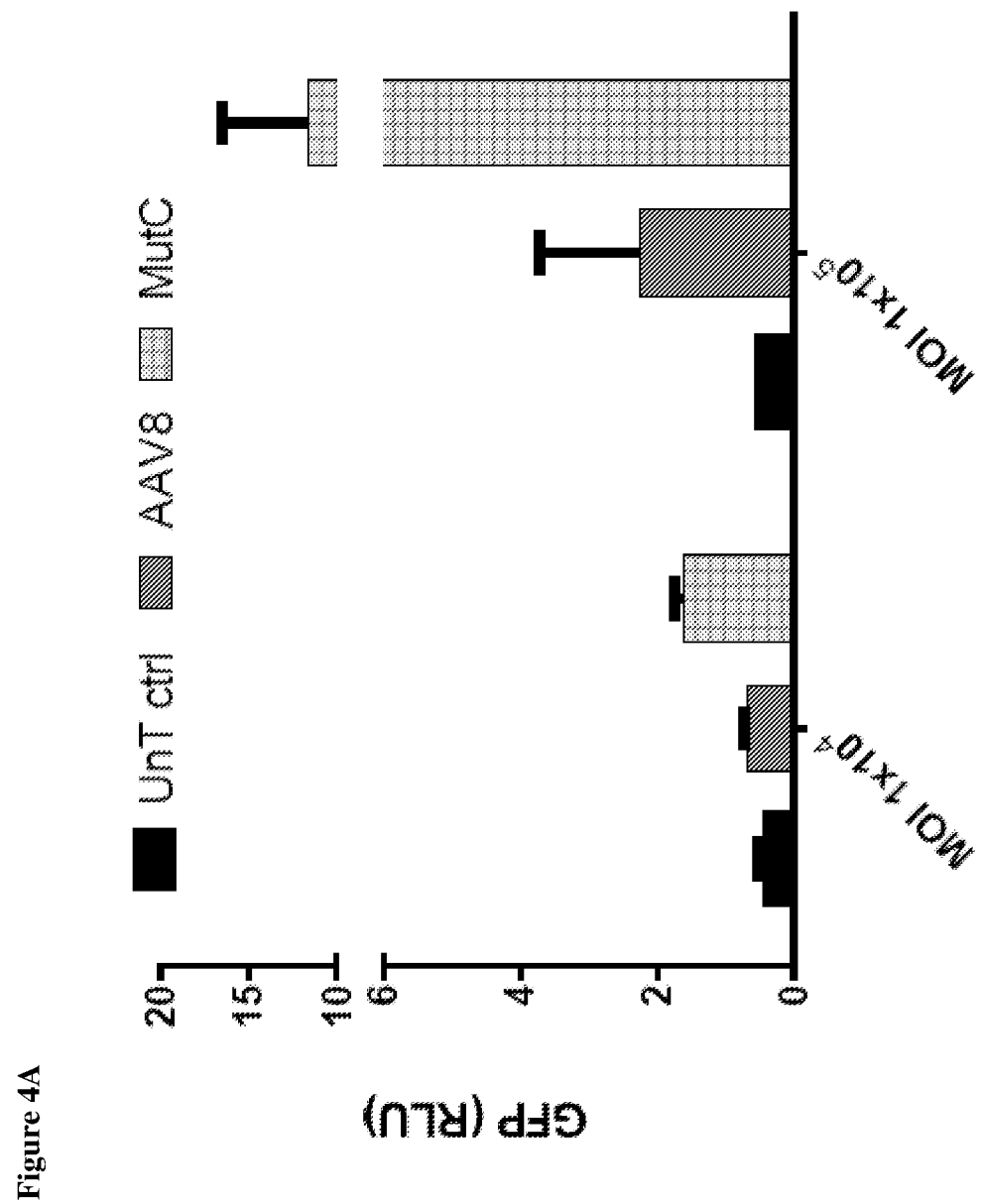
FIG. 4A shows the GFP excitation/emission at 485 nm/535 nm resulting from transduction of 3D cultures of HepG2 cells with AAV8 and AAV Mutant C vectors containing a GFP gene at a MOI of $1 \times 10^4$ or $1 \times 10^5$.
Figure 4B:
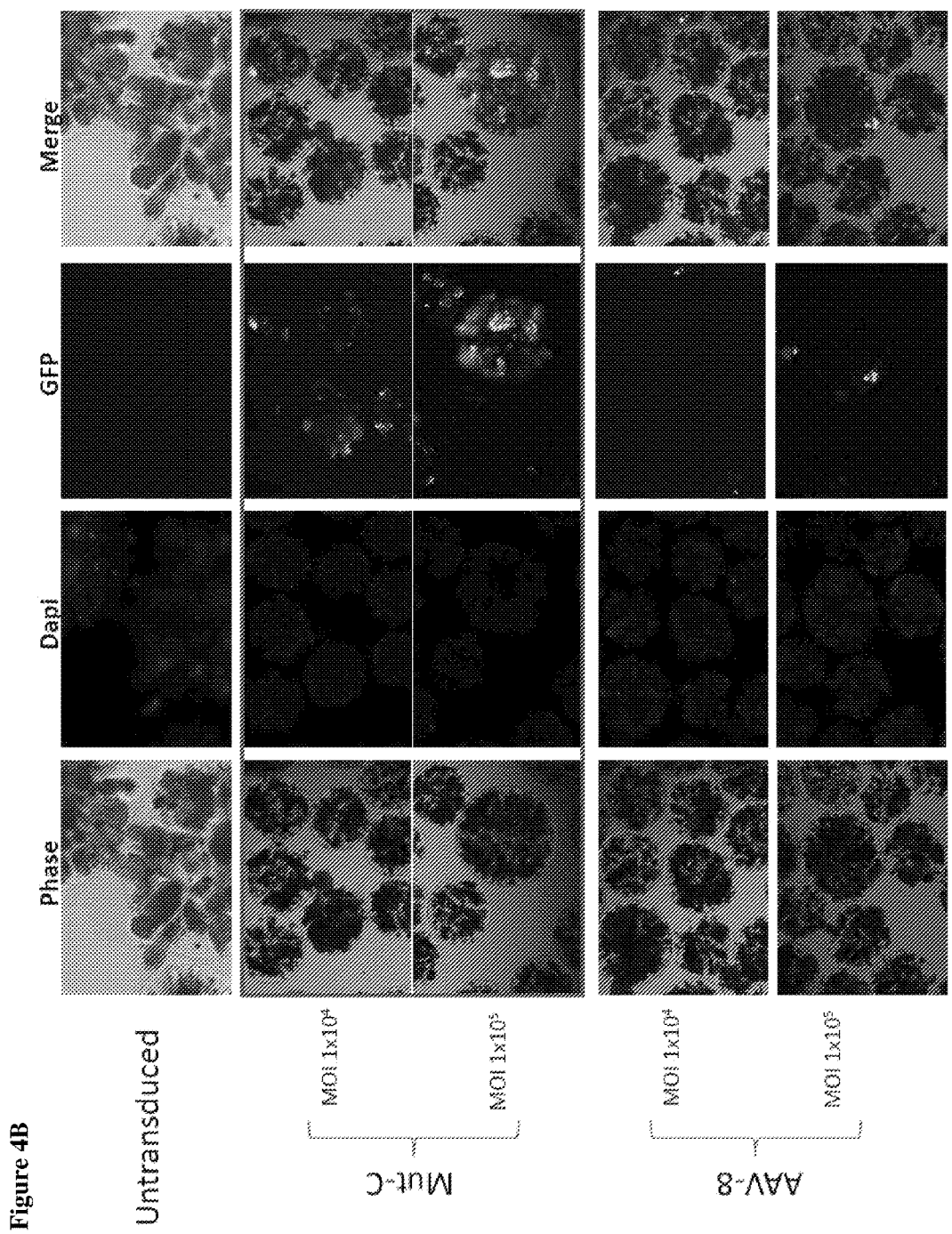
FIG. 4B is fluorescent microscope images of the transduced 3D HepG2 cells (5× objective, GFP exposure time constant [300 ms]).
Figure 5:
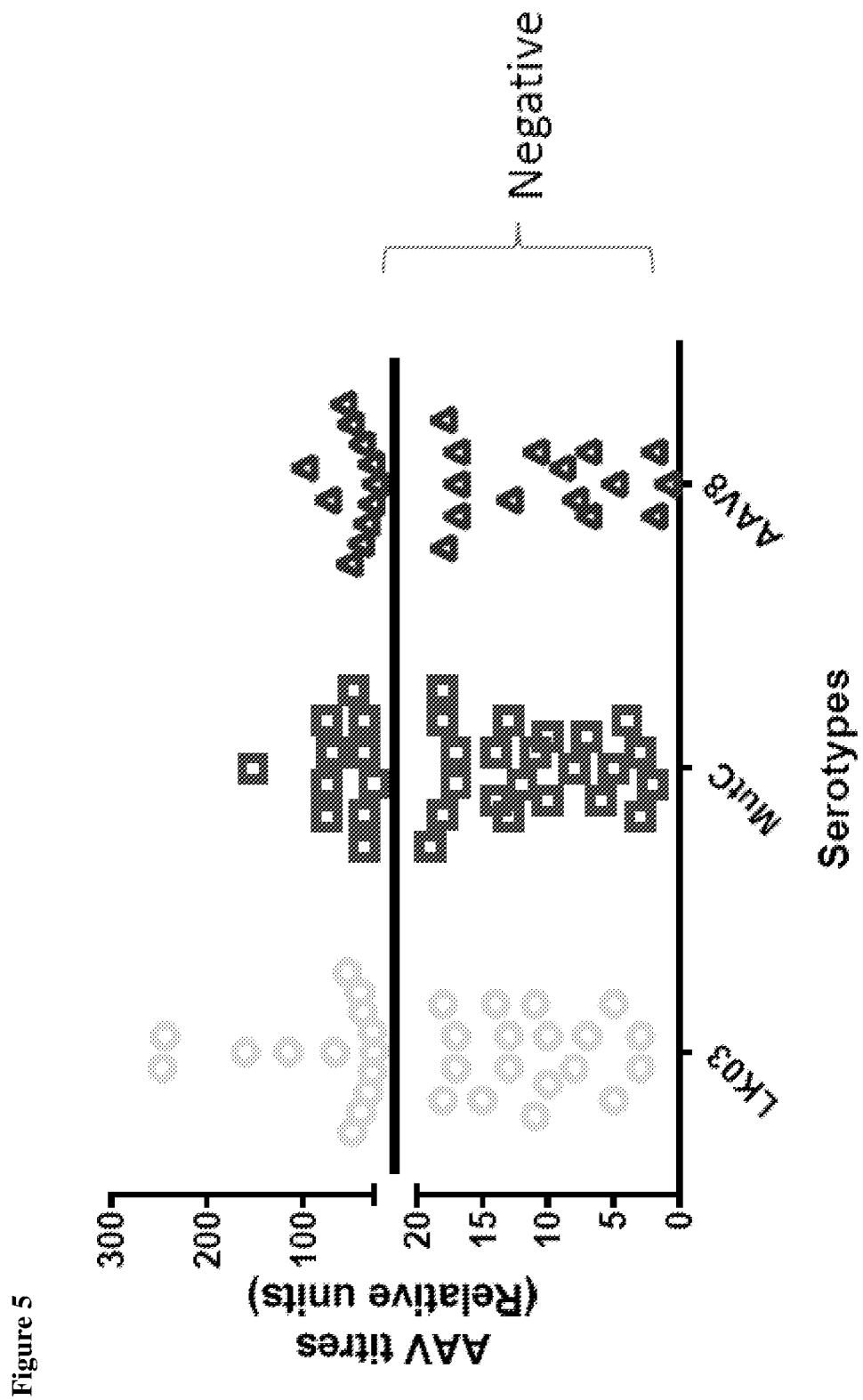
FIG. 5 shows the prevalence of antibodies to AAV vectors in severe haemophilia patients as a result of an ELISA immune-adsorption method.

The 3D bead cultures were transduced with either AAV8 or AAV Mut C at an MOI of $1\times10^4$ or $1\times10^5$ using a vector containing the CMV GFP expression cassette. As before transduction efficiency was determined by quantify green fluorescence using a plate reader (FIG. 4A) or direct fluorescent microscopy (FIG. 4B). A 3-5 fold higher gene transfer efficiency of the 3D spheroids was observed with AAV Mut C when compared to GFP expression in beads transduced with AAV8. This difference in gene transfer efficiency was also noted using direct florescent microscopy.

Assessment of Pre-Existing Antibodies Against Mutant C in Severe Haemophilia Patients Plasma samples from unselected severe haemophilia patients were screened to assess the prevalence of pre-existing antibodies against AAV Mut C using an ELISA immune-adsorption method. 63% of the patients displayed no detectable antibodies against AAV Mut C. The corresponding levels for AAV8 and AAV-LK03 were 51%. This therefore suggests that fewer patients with severe haemophilia have antibodies to AAV Mut C.

The invention claimed is:

1. An AAV capsid protein comprising an amino acid sequence
    i) having the sequence of SEQ ID NO: 3; or
    ii) having at least 99% identity to SEQ ID NO: 3 and is a hybrid capsid comprising regions of the AAV3B and AAV8 capsids.

2. The AAV capsid protein of claim 1, wherein the amino acid sequence has at least 99.5% identity to SEQ ID NO: 3.

3. The AAV capsid protein of claim 1, wherein the amino acid sequence has the sequence of SEQ ID NO: 3.

4. A polynucleotide encoding the capsid protein of claim 1.

5. A viral particle comprising the capsid protein of claim 1.

6. A pharmaceutical composition comprising the capsid protein of claim 1, and one or more pharmaceutically acceptable excipients.

* * * * *

SEQUENCE LISTING

<160> NUMBER OF SEQ ID NOS: 6

<210> SEQ ID NO 1
<211> LENGTH: 738
<212> TYPE: PRT
<213> ORGANISM: Artificial Sequence
<220> FEATURE:
<223> OTHER INFORMATION: AAV-LK03, AAV5 and AAV8 derived capsid protein (Mut A)

<400> SEQUENCE: 1

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

-continued

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510

Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Ile Lys Thr Thr Asn Pro Val Ala Thr
                565                 570                 575

Glu Glu Tyr Gly Ile Val Ala Asp Asn Leu Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu

<210> SEQ ID NO 2
<211> LENGTH: 725
<212> TYPE: PRT
<213> ORGANISM: Artificial Sequence
<220> FEATURE:
<223> OTHER INFORMATION: AAV-LK03, AAV5 and AAV8 derived capsid protein (Mut B)

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
            85                  90                  95

Asp Ala Glu Phe Gln Glu Arg Leu Lys Glu Asp Thr Ser Phe Gly Gly
        100                 105                 110

Asn Leu Gly Arg Ala Val Phe Gln Ala Lys Lys Arg Leu Leu Glu Pro
    115                 120                 125

Leu Gly Leu Val Glu Glu Ala Ala Lys Thr Ala Pro Thr Gly Lys Arg
130                 135                 140

Ile Asp Asp His Phe Pro Lys Arg Lys Lys Ala Arg Thr Glu Glu Asp
145                 150                 155                 160

Ser Lys Pro Ser Thr Ser Ser Asp Ala Glu Ala Gly Pro Ser Gly Ser
                165                 170                 175

Gln Gln Leu Gln Ile Pro Ala Gln Pro Ala Ser Ser Leu Gly Ala Asp
            180                 185                 190

Thr Met Ser Ala Gly Gly Gly Pro Leu Gly Asp Asn Asn Gln Gly
        195                 200                 205

Ala Asp Gly Val Gly Asn Ala Ser Gly Asp Trp His Cys Asp Ser Thr
    210                 215                 220

Trp Met Gly Asp Arg Val Val Thr Lys Ser Thr Arg Thr Trp Val Leu
225                 230                 235                 240

Pro Ser Tyr Asn Asn His Gln Tyr Arg Glu Ile Lys Ser Gly Ser Val
                245                 250                 255

Asp Gly Ser Asn Ala Asn Ala Tyr Phe Gly Tyr Ser Thr Pro Trp Gly
            260                 265                 270

Tyr Phe Asp Phe Asn Arg Phe His Ser His Trp Ser Pro Arg Asp Trp
        275                 280                 285

Gln Arg Leu Ile Asn Asn Tyr Trp Gly Phe Arg Pro Arg Ser Leu Arg
    290                 295                 300

Val Lys Ile Phe Asn Ile Gln Val Lys Glu Val Thr Val Gln Asp Ser
305                 310                 315                 320

Thr Thr Thr Ile Ala Asn Asn Leu Thr Ser Thr Val Gln Val Phe Thr
                325                 330                 335

Asp Asp Asp Tyr Gln Leu Pro Tyr Val Val Gly Asn Gly Thr Glu Gly
            340                 345                 350

Cys Leu Pro Ala Phe Pro Pro Gln Val Phe Thr Leu Pro Gln Tyr Gly
        355                 360                 365

Tyr Ala Thr Leu Asn Arg Asp Asn Thr Glu Asn Pro Thr Glu Arg Ser
    370                 375                 380

Ser Phe Phe Cys Leu Glu Tyr Phe Pro Ser Lys Met Leu Arg Thr Gly
```

-continued

```
                385                 390                 395                 400
        Asn Asn Phe Glu Phe Thr Tyr Asn Phe Glu Glu Val Pro Phe His Ser
                        405                 410                 415

Ser Phe Ala Pro Ser Gln Asn Leu Phe Lys Leu Ala Asn Pro Leu Val
                        420                 425                 430

Asp Gln Tyr Leu Tyr Arg Phe Val Ser Thr Asn Asn Thr Gly Gly Val
                        435                 440                 445

Gln Phe Asn Lys Asn Leu Ala Gly Arg Tyr Ala Asn Thr Tyr Lys Asn
                        450                 455                 460

Trp Phe Pro Gly Pro Met Gly Arg Thr Gln Gly Trp Asn Leu Gly Ser
        465                 470                 475                 480

Gly Val Asn Arg Ala Ser Val Ser Ala Phe Ala Thr Thr Asn Arg Met
                        485                 490                 495

Glu Leu Glu Gly Ala Ser Tyr Gln Val Pro Pro Gln Pro Asn Gly Met
                        500                 505                 510

Thr Asn Asn Leu Gln Gly Ser Asn Thr Tyr Ala Leu Glu Asn Thr Met
                        515                 520                 525

Ile Phe Asn Ser Gln Pro Ala Asn Pro Gly Thr Thr Ala Thr Tyr Leu
                        530                 535                 540

Glu Gly Asn Met Leu Ile Thr Ser Glu Ser Glu Thr Gln Pro Val Asn
        545                 550                 555                 560

Arg Val Ala Tyr Asn Val Gly Gly Gln Met Ala Thr Asn Asn Gln Ser
                        565                 570                 575

Ser Thr Thr Ala Pro Ala Thr Gly Thr Tyr Asn Leu Gln Glu Ile Val
                        580                 585                 590

Pro Gly Ser Val Trp Met Glu Arg Asp Val Tyr Leu Gln Gly Pro Ile
                        595                 600                 605

Trp Ala Lys Ile Pro Glu Thr Gly Ala His Phe His Pro Ser Pro Ala
                        610                 615                 620

Met Gly Gly Phe Gly Leu Lys His Pro Pro Met Met Leu Ile Lys
        625                 630                 635                 640

Asn Thr Pro Val Pro Gly Asn Ile Thr Ser Phe Ser Asp Val Pro Val
                        645                 650                 655

Ser Ser Phe Ile Thr Gln Tyr Ser Thr Gly Gln Val Thr Val Glu Met
                        660                 665                 670

Glu Trp Glu Leu Lys Lys Glu Asn Ser Lys Arg Trp Asn Pro Glu Ile
                        675                 680                 685

Gln Tyr Thr Asn Asn Tyr Asn Asp Pro Gln Phe Val Asp Phe Ala Pro
                        690                 695                 700

Asp Ser Thr Gly Glu Tyr Arg Thr Thr Arg Pro Ile Gly Thr Arg Tyr
        705                 710                 715                 720

Leu Thr Arg Pro Leu
                        725

<210> SEQ ID NO 3
<211> LENGTH: 736
<212> TYPE: PRT
<213> ORGANISM: Artificial Sequence
<220> FEATURE:
<223> OTHER INFORMATION: AAV3B and AAV8 derived capsid protein (Mut C)

<400> SEQUENCE: 3

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
```

20                  25                  30
Lys Ala Asn Gln Gln Lys Gln Asp Asp Gly Arg Gly Leu Val Leu Pro
            35                  40                  45
Gly Tyr Lys Tyr Leu Gly Pro Phe Asn Gly Leu Asp Lys Gly Glu Pro
        50                  55                  60
Val Asn Ala Ala Asp Ala Ala Leu Glu His Asp Lys Ala Tyr Asp
65                  70                  75                  80
Gln Gln Leu Gln Ala Gly Asp Asn Pro Tyr Leu Arg Tyr Asn His Ala
                85                  90                  95
Asp Ala Glu Phe Gln Glu Arg Leu Gln Glu Asp Thr Ser Phe Gly Gly
            100                 105                 110
Asn Leu Gly Arg Ala Val Phe Gln Ala Lys Lys Arg Val Leu Glu Pro
        115                 120                 125
Leu Gly Leu Val Glu Glu Gly Ala Lys Thr Ala Pro Gly Lys Lys Arg
    130                 135                 140
Pro Val Asp Gln Ser Pro Gln Glu Pro Asp Ser Ser Ser Gly Val Gly
145                 150                 155                 160
Lys Ser Gly Lys Gln Pro Ala Arg Lys Arg Leu Asn Phe Gly Gln Thr
                165                 170                 175
Gly Asp Ser Glu Ser Val Pro Asp Pro Gln Pro Leu Gly Glu Pro Pro
            180                 185                 190
Ala Ala Pro Thr Ser Leu Gly Ser Asn Thr Met Ala Ser Gly Gly Gly
        195                 200                 205
Ala Pro Met Ala Asp Asn Asn Glu Gly Ala Asp Gly Val Gly Asn Ser
    210                 215                 220
Ser Gly Asn Trp His Cys Asp Ser Gln Trp Leu Gly Asp Arg Val Ile
225                 230                 235                 240
Thr Thr Ser Thr Arg Thr Trp Ala Leu Pro Thr Tyr Asn Asn His Leu
                245                 250                 255
Tyr Lys Gln Ile Ser Ser Gln Ser Gly Ala Ser Asn Asp Asn His Tyr
            260                 265                 270
Phe Gly Tyr Ser Thr Pro Trp Gly Tyr Phe Asp Phe Asn Arg Phe His
        275                 280                 285
Cys His Phe Ser Pro Arg Asp Trp Gln Arg Leu Ile Asn Asn Asn Trp
    290                 295                 300
Gly Phe Arg Pro Lys Lys Leu Ser Phe Lys Leu Phe Asn Ile Gln Val
305                 310                 315                 320
Lys Glu Val Thr Gln Asn Asp Gly Thr Thr Thr Ile Ala Asn Asn Leu
                325                 330                 335
Thr Ser Thr Val Gln Val Phe Thr Asp Ser Glu Tyr Gln Leu Pro Tyr
            340                 345                 350
Val Leu Gly Ser Ala His Gln Gly Cys Leu Pro Pro Phe Pro Ala Asp
        355                 360                 365
Val Phe Met Val Pro Gln Tyr Gly Tyr Leu Thr Leu Asn Asn Gly Ser
    370                 375                 380
Gln Ala Val Gly Arg Ser Ser Phe Tyr Cys Leu Glu Tyr Phe Pro Ser
385                 390                 395                 400
Gln Met Leu Arg Thr Gly Asn Asn Phe Gln Phe Ser Tyr Thr Phe Glu
                405                 410                 415
Asp Val Pro Phe His Ser Ser Tyr Ala His Ser Gln Ser Leu Asp Arg
            420                 425                 430
Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
            450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
610                 615                 620

Thr Asp Gly His Phe His Pro Ser Pro Leu Met Gly Gly Phe Gly Leu
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Asn Leu
                725                 730                 735

<210> SEQ ID NO 4
<211> LENGTH: 735
<212> TYPE: PRT
<213> ORGANISM: Artificial Sequence
<220> FEATURE:
<223> OTHER INFORMATION: AAV3B and AAV5 derived capsid protein (Mut D)

<400> SEQUENCE: 4

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

```
Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Gly Lys Lys Arg Pro
    130                 135                 140

Val Asp Gln Ser Pro Gln Glu Pro Asp Ser Ser Gly Val Gly Lys
145                 150                 155                 160

Ser Gly Lys Gln Pro Ala Arg Lys Arg Leu Asn Phe Gly Gln Thr Gly
                165                 170                 175

Asp Ser Glu Ser Val Pro Asp Pro Gln Pro Leu Gly Glu Pro Pro Ala
            180                 185                 190

Ala Pro Thr Ser Leu Gly Ser Asn Thr Met Ala Ser Gly Gly Gly Ala
        195                 200                 205

Pro Met Ala Asp Asn Asn Glu Gly Ala Asp Gly Val Gly Asn Ser Ser
    210                 215                 220

Gly Asn Trp His Cys Asp Ser Gln Trp Leu Gly Asp Arg Val Ile Thr
225                 230                 235                 240

Thr Ser Thr Arg Thr Trp Ala Leu Pro Thr Tyr Asn Asn His Leu Tyr
                245                 250                 255

Lys Gln Ile Ser Ser Gln Ser Gly Ala Ser Asn Asp Asn His Tyr Phe
            260                 265                 270

Gly Tyr Ser Thr Pro Trp Gly Tyr Phe Asp Phe Asn Arg Phe His Cys
        275                 280                 285

His Phe Ser Pro Arg Asp Trp Gln Arg Leu Ile Asn Asn Asn Trp Gly
    290                 295                 300

Phe Arg Pro Lys Lys Leu Ser Phe Lys Leu Phe Asn Ile Gln Val Lys
305                 310                 315                 320

Glu Val Thr Gln Asn Asp Gly Thr Thr Thr Ile Ala Asn Asn Leu Thr
                325                 330                 335

Ser Thr Val Gln Val Phe Thr Asp Ser Glu Tyr Gln Leu Pro Tyr Val
            340                 345                 350

Leu Gly Ser Ala His Gln Gly Cys Leu Pro Pro Phe Pro Ala Asp Val
        355                 360                 365

Phe Met Val Pro Gln Tyr Gly Tyr Leu Thr Leu Asn Asn Gly Ser Gln
    370                 375                 380

Ala Val Gly Arg Ser Ser Phe Tyr Cys Leu Glu Tyr Phe Pro Ser Gln
385                 390                 395                 400

Met Leu Arg Thr Gly Asn Asn Phe Gln Phe Ser Tyr Thr Phe Glu Asp
                405                 410                 415

Val Pro Phe His Ser Ser Tyr Ala His Ser Gln Ser Leu Asp Arg Leu
            420                 425                 430

Met Asn Pro Leu Ile Asp Gln Tyr Leu Tyr Tyr Leu Asn Arg Thr Gln
        435                 440                 445

Gly Thr Thr Ser Gly Thr Thr Asn Gln Ser Arg Leu Leu Phe Ser Gln
    450                 455                 460

Ala Gly Pro Gln Ser Met Ser Leu Gln Ala Arg Asn Trp Leu Pro Gly
465                 470                 475                 480

Pro Cys Tyr Arg Gln Gln Arg Leu Ser Lys Thr Ala Asn Asp Asn Asn
                485                 490                 495
```

```
Asn Ser Asn Phe Pro Trp Thr Ala Ala Ser Lys Tyr His Leu Asn Gly
                500                 505                 510

Arg Asp Ser Leu Val Asn Pro Gly Pro Ala Met Ala Ser His Lys Asp
            515                 520                 525

Asp Glu Glu Lys Phe Phe Pro Met His Gly Asn Leu Ile Phe Gly Lys
        530                 535                 540

Glu Gly Thr Thr Ala Ser Asn Ala Glu Leu Asp Asn Val Met Ile Thr
545                 550                 555                 560

Asp Glu Glu Glu Ile Arg Thr Thr Asn Pro Val Ala Thr Glu Gln Tyr
                565                 570                 575

Gly Thr Val Ala Asn Asn Leu Gln Ser Ser Asn Thr Ala Pro Thr Thr
            580                 585                 590

Arg Thr Val Asn Asp Gln Gly Ala Leu Pro Gly Met Val Trp Gln Asp
        595                 600                 605

Arg Asp Val Tyr Leu Gln Gly Pro Ile Trp Ala Lys Ile Pro His Thr
610                 615                 620

Asp Gly His Phe His Pro Ser Pro Leu Met Gly Gly Phe Gly Leu Lys
625                 630                 635                 640

His Pro Pro Pro Gln Ile Met Ile Lys Asn Thr Pro Val Pro Ala Asn
                645                 650                 655

Pro Pro Thr Thr Phe Ser Pro Ala Lys Phe Ala Ser Phe Ile Thr Gln
            660                 665                 670

Tyr Ser Thr Gly Gln Val Ser Val Glu Ile Glu Trp Glu Leu Gln Lys
        675                 680                 685

Glu Asn Ser Lys Arg Trp Asn Pro Glu Ile Gln Tyr Thr Ser Asn Tyr
690                 695                 700

Asn Lys Ser Val Asn Val Asp Phe Thr Val Asp Thr Asn Gly Val Tyr
705                 710                 715                 720

Ser Glu Pro Arg Pro Ile Gly Thr Arg Tyr Leu Thr Arg Pro Leu
                725                 730                 735

<210> SEQ ID NO 5
<211> LENGTH: 736
<212> TYPE: PRT
<213> ORGANISM: Artificial Sequence
<220> FEATURE:
<223> OTHER INFORMATION: AAV3B and AAV8 derived capsid protein (Mut E)

<400> SEQUENCE: 5

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125
```

```
Leu Gly Leu Val Glu Glu Gly Ala Lys Thr Ala Pro Gly Lys Lys Arg
130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
                260                 265                 270

Tyr Phe Gly Tyr Ser Thr Pro Trp Gly Tyr Phe Asp Phe Asn Arg Phe
            275                 280                 285

His Cys His Phe Ser Pro Arg Asp Trp Gln Arg Leu Ile Asn Asn Asn
        290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
                340                 345                 350

Tyr Val Leu Gly Ser Ala His Gln Gly Cys Leu Pro Pro Phe Pro Ala
            355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
                420                 425                 430

Arg Leu Met Asn Pro Leu Ile Asp Gln Tyr Leu Tyr Tyr Leu Ser Arg
            435                 440                 445

Thr Gln Thr Thr Gly Gly Thr Ala Asn Thr Gln Thr Leu Gly Phe Ser
        450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
                500                 505                 510

Gly Arg Asn Ser Leu Ala Asn Pro Gly Ile Ala Met Ala Thr His Lys
            515                 520                 525

Asp Asp Glu Glu Arg Phe Phe Pro Ser Asn Gly Ile Leu Ile Phe Gly
        530                 535                 540

Lys Gln Gly Thr Thr Ala Ser Asn Ala Glu Leu Asp Asn Val Met Ile
```

```
                        545                 550                 555                 560
                Thr Asp Glu Glu Glu Ile Lys Thr Thr Asn Pro Val Ala Thr Glu Glu
                                565                 570                 575

Tyr Gly Ile Val Ala Asp Asn Leu Gln Gln Gln Asn Thr Ala Pro Gln
                                580                 585                 590

Ile Gly Thr Val Asn Ser Gln Gly Ala Leu Pro Gly Met Val Trp Gln
                                595                 600                 605

Asn Arg Asp Val Tyr Leu Gln Gly Pro Ile Trp Ala Lys Ile Pro His
                            610                 615                 620

Thr Asp Gly Asn Phe His Pro Ser Pro Leu Met Gly Gly Phe Gly Leu
                625                 630                 635                 640

Lys His Pro Pro Pro Gln Ile Leu Ile Lys Asn Thr Pro Val Pro Ala
                                645                 650                 655

Asp Pro Pro Thr Thr Phe Asn Gln Ser Lys Leu Asn Ser Phe Ile Thr
                                660                 665                 670

Gln Tyr Ser Thr Gly Gln Val Ser Val Glu Ile Glu Trp Glu Leu Gln
                                675                 680                 685

Lys Glu Asn Ser Lys Arg Trp Asn Pro Glu Ile Gln Tyr Thr Ser Asn
                            690                 695                 700

Tyr Asn Lys Ser Val Asn Val Asp Phe Thr Val Asp Thr Asn Gly Val
                705                 710                 715                 720

Tyr Ser Glu Pro Arg Pro Ile Gly Thr Arg Tyr Leu Thr Arg Asn Leu
                                725                 730                 735

<210> SEQ ID NO 6
<211> LENGTH: 736
<212> TYPE: PRT
<213> ORGANISM: Artificial Sequence
<220> FEATURE:
<223> OTHER INFORMATION: AAV3B and AAV8 derived capsid protein (Mut F)

<400> SEQUENCE: 6

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Lys Pro
                20                  25                  30

Lys Ala Asn Gln Gln Lys Gln Asp Asp Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
                100                 105                 110

Asn Leu Gly Arg Ala Val Phe Gln Ala Lys Lys Arg Val Leu Glu Pro
            115                 120                 125

Leu Gly Leu Val Glu Glu Gly Ala Lys Thr Ala Pro Gly Lys Lys Arg
        130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
```

```
            180                 185                 190
Pro Ala Ala Pro Ser Gly Val Gly Pro Asn Thr Met Ala Ala Gly Gly
            195                 200                 205

Gly Ala Pro Met Ala Asp Asn Asn Glu Gly Ala Asp Gly Val Gly Ser
        210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Gln Ser Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
        290                 295                 300

Trp Gly Phe Arg Pro Lys Arg Leu Ser Phe Lys Leu Phe Asn Ile Gln
305                 310                 315                 320

Val Lys Glu Val Thr Gln Asn Glu Gly Thr Lys Thr Ile Ala Asn Asn
                325                 330                 335

Leu Thr Ser Thr Ile Gln Val Phe Thr Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
        370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Gln Phe Thr Tyr Thr Phe
                405                 410                 415

Glu Asp Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Ser Arg
        435                 440                 445

Thr Gln Thr Thr Gly Gly Thr Ala Asn Thr Gln Thr Leu Gly Phe Ser
        450                 455                 460

Gln Gly Gly Pro Asn Thr Met Ala Asn Gln Ala Lys Asn Trp Leu Pro
465                 470                 475                 480

Gly Pro Cys Tyr Arg Gln Gln Arg Val Ser Thr Thr Thr Gly Gln Asn
                485                 490                 495

Asn Asn Ser Asn Phe Ala Trp Thr Ala Gly Thr Lys Tyr His Leu Asn
            500                 505                 510

Gly Arg Asn Ser Leu Ala Asn Pro Gly Ile Ala Met Ala Thr His Lys
        515                 520                 525

Asp Asp Glu Glu Arg Phe Phe Pro Ser Asn Gly Ile Leu Ile Phe Gly
        530                 535                 540

Lys Gln Asn Ala Ala Arg Asp Asn Ala Asp Tyr Ser Asp Val Met Leu
545                 550                 555                 560

Thr Ser Glu Glu Glu Ile Lys Thr Thr Asn Pro Val Ala Thr Glu Glu
                565                 570                 575

Tyr Gly Ile Val Ala Asp Asn Leu Gln Gln Gln Asn Thr Ala Pro Gln
            580                 585                 590

Ile Gly Thr Val Asn Ser Gln Gly Ala Leu Pro Gly Met Val Trp Gln
        595                 600                 605
```

```
Asn Arg Asp Val Tyr Leu Gln Gly Pro Ile Trp Ala Lys Ile Pro His
    610             615             620
Thr Asp Gly Asn Phe His Pro Ser Pro Leu Met Gly Gly Phe Gly Leu
625             630             635             640
Lys His Pro Pro Gln Ile Leu Ile Lys Asn Thr Pro Val Pro Ala
            645             650             655
Asp Pro Pro Thr Thr Phe Asn Gln Ser Lys Leu Asn Ser Phe Ile Thr
            660             665             670
Gln Tyr Ser Thr Gly Gln Val Ser Val Glu Ile Glu Trp Glu Leu Gln
        675             680             685
Lys Glu Asn Ser Lys Arg Trp Asn Pro Glu Ile Gln Tyr Thr Ser Asn
        690             695             700
Tyr Tyr Lys Ser Thr Ser Val Asp Phe Ala Val Asn Thr Glu Gly Val
705             710             715             720
Tyr Ser Glu Pro Arg Pro Ile Gly Thr Arg Tyr Leu Thr Arg Asn Leu
            725             730             735
```